United States Patent [19]
O'Donnell, Jr.

[11] Patent Number: 5,460,627
[45] Date of Patent: Oct. 24, 1995

[54] METHOD OF EVALUATING A LASER USED IN OPHTHALMOLOGICAL SURGERY

[76] Inventor: Francis E. O'Donnell, Jr., 709 The Hamptons, Town & Country, Mo. 63017

[21] Appl. No.: 269,139

[22] Filed: Jun. 30, 1994

Related U.S. Application Data

[63] Continuation-in-part of Ser. No. 55,578, May 3, 1993.
[51] Int. Cl.$^6$ ........................ A61N 5/02
[52] U.S. Cl. .............. 606/4; 606/10; 606/2; 128/898
[58] Field of Search ............ 606/1–19; 128/847, 128/898; 336/121, 213

[56] References Cited

U.S. PATENT DOCUMENTS

| | | | |
|---|---|---|---|
| 4,461,294 | 7/1984 | Baron | 606/4 |
| 4,669,466 | 6/1987 | L'Esperance | 606/5 |
| 4,676,790 | 6/1987 | Kern | 606/4 |
| 5,163,934 | 11/1992 | Munnerlyn | 606/4 |
| 5,261,822 | 11/1993 | Hall et al. | 356/121 |

*Primary Examiner*—David M. Shay
*Attorney, Agent, or Firm*—Paul M. Denk

[57] ABSTRACT

A method of using rastophotogrammetry and Placido-disc videokeratoscopy in ophthalmological surgery to calibrate a surgical laser wherein the effect of laser ablation on various substrates is measured by performing rastophotogrammetry or Placido-disc videokeratoscopy on the substrate before and after laser ablation to determine whether there is a uniform ablation and no unwanted effects created by the laser. The substrate can be calibration block, an intraoccular lens implant, a contact lens, an artificial cornea, or cornea.

2 Claims, 3 Drawing Sheets

5,460,627

METHOD OF EVALUATING A LASER USED IN OPHTHALMOLOGICAL SURGERY

This application is a continuation-in-part of application Ser. No. 08/055,578, filed May 3, 1993.

BACKGROUND OF THE INVENTION

This invention relates to a method of using rastophotogrammetry and Placido-disc video keratoscopy in ophthalmological surgery, more specifically, to a method of using rastophotogrammetry and Placido-disc video keratoscopy to evaluate a laser used in refractive surgery so as to measure the amount of unwanted lens effect delivered by an excimer laser or other ultraviolet or infrared laser beams.

Rastophotogrammetry has been used in ophthalmological surgery to measure the surface contour of the optic nerve head and to measure corneal surface curvatures. In the technique of rastophotogrammetry a series of parallel lines or a grid is projected on the surface to measured. Computerized digital analysis of a video image is performed to detect elevations or depressions of the surface being measured. Rastostereographic imaging is combined with image processing computer software to produce a model of the topography of the cornea, for example.

Prior art uses of the technique have been limited to measuring epithelialized corneal surfaces, before and after refractive procedures such as radialkeratotomy and excimer photo-refractive keratoscope. Although useful, prior art applications of the technique only measure epithelialized corneal topography before and after surgical intervention. There is no predictive value in this technique, that is, the rastophotogram only measures changes in the corneal topography retrospectively. If the laser used during surgery is not properly calibrated, the laser may have unwanted lens effect by removing corneal tissue in an uneven pattern leaving depressions (hot spots) or elevations (cold spots). The goal of the surgery is to perform a uniform ablation with a uniform laser beam, i.e,. a laser beam having no unwanted lens effect. Furthermore, the prior art uses of rastophotogrammetry do not measure topographical changes in optic implants or on contact lenses.

Recently it has been determined that Placido-disc videokeratoscopy can be used to determine surface contour, particularly to visualize and determine the surface contour of an "Contact lens" or artificial cornea. The Placido-disc video keratoscope is a type of computerized videokeratography now available to ohthalmological surgeons. The instrument allows the surgeon to measure and modify corneal curvature. The basic videokeratograph instrument includes a light source projected onto the cornea. The modification of the light by the cornea is captured by a video camera and the information is analyzed by computer software. The data is displayed in a variety of formats including photographs and on a screen.

The Placido-disc imaging is an extension of the single mire used in the keratomoter. A series of rings is projected onto the cornea, and the reflected images are detected by a video camera. Curvature data is derived from the measured distances between the rings. The patient is placed before a corneascope projecting a 16-ring conical Placido-disc. The scope is positioned in front of the cornea. The instrument contains a video camera for image capture. The computer digitalizes or converts the data obtained from the video output into a form that can be analyzed. A number of highly sophisticated programs convert the data into a series of color graphics displays. Hard copies can be obtained from a color printer or a camera. The color graphics provide topographic maps. Systems currently commercially available include the EyeSys Corneal Analysis System (CAS) (EyeSys Laboratories) and the Topographic Modeling System (TMS) (Computed Anatomy, Inc). Although Placido-disc videokeratoscopy systems work poorly on deepithelialized cornea after radial keratotomy, they can be used to evaluate the effect of laser ablation on an artificial cornea.

SUMMARY OF THE INVENTION

It is, therefore, an object of the method of the present invention to use rastophotogrammetry to evaluate a surgical laser to prevent unwanted lens effect.

It is another object of the present invention to provide a method of using Placido-disc videokeratoscopy to evaluate a surgical laser.

Yet another object of the present invention is to provide a method of using rastophotogrammetry or Placido-disc videokeratoscopy before and after a laser ablation to confirm a uniform laser beam.

Still another object of the present invention is to provide a method of confirming the desire lens effect of the laser beam on a calibration block.

Yet another object of the present invention is to provide a method of quantifying the change in optic curvature of an intraoccular lens implant before and after laser treatment to alter the refractive power.

It is another object of the present invention to provide a method of using Placido-disc video keratoscopy to evaluate a surgical laser.

Still another object of the present invention is to provide a method of evaluating a laser using an artificial cornea of a known dioptric power employing Placido-disc keratoscopy to measure the curvature of the artificial cornea to determine the effect of the laser beam on the artificial cornea.

Yet another object of the present invention is to provide a method of performing ophthalmological surgery in which a rastophotogrammetry is performed on a deepithelialized cornea so as to measure the topography of the deepithelialized cornea before and after laser ablation of the cornea.

Briefly stated, a method of evaluating an eye surgery laser is provided wherein the effect of the laser ablation on various substrates is measured by performing rastophotogrammetry or Placido-disc videokeratoscopy on the substrate before, during, and after laser ablation to determine whether there is a uniform ablation and no unwanted effect. The substrate can be a calibration block, and intraoccular lens implant, a contact lens, an artificial cornea or a human cornea.

DESCRIPTION OF THE PREFERRED EMBODIMENT

Figure 1:
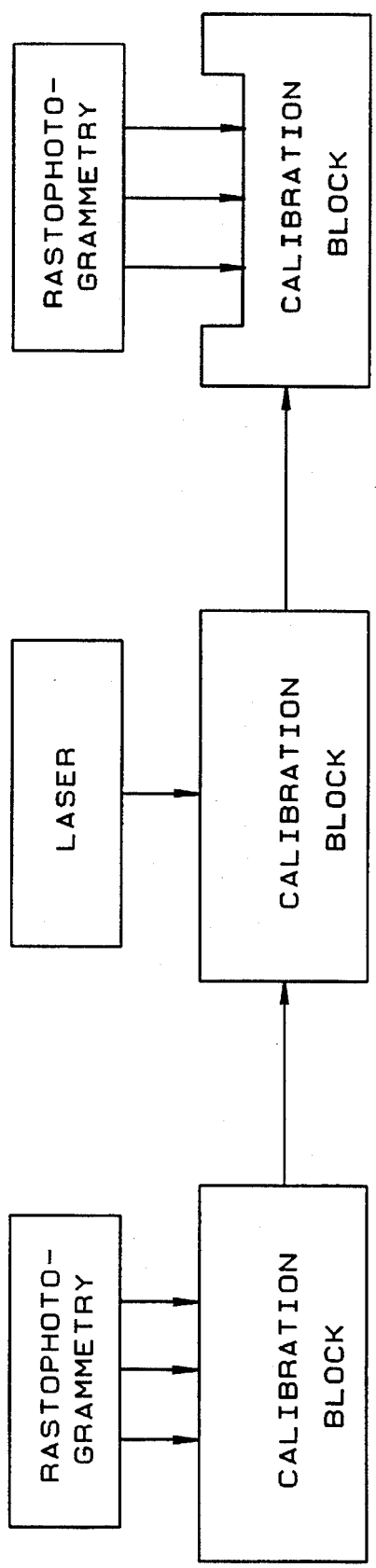
FIG. 1 is a diagram illustrating the use of rastophotogrammetry to determine unwanted lens effect (i.e., hot or cold spots) of a laser beam.

As illustrated in FIG. 1, rastophotogrammetry is used to determine the amount of unwanted lens effect delivered by an excimer or other ultraviolet or infrared laser beam.

Rastophotogrammetry device used is as the type marketed by PAR Technology Corporation, Hartford, N.Y. 13413. A calibration block, typically made of polymethylmethachrylate, is employed. The rastophotogrammetry is used before calibration to evaluate the laser beam. A rastophotogram is made of the calibration block, the laser is applied to the calibration block, and a rastophotogram is performed to see if the laser effect is a uniform ablation with no depressions (hot spots) or elevations (cold spots). As illustrated in FIG. 1, the rastophotogram confirms a uniform ablation of the calibration block.

Figure 2:
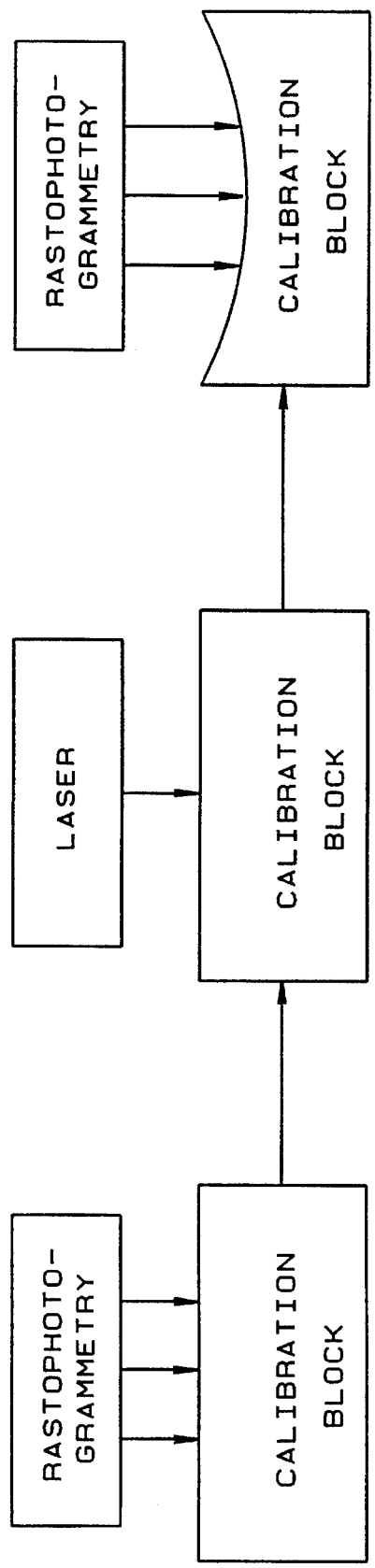
FIG. 2 is a diagram demonstrating the use of rastophotogrammetry to confirm the desired lens effect of a laser beam.

Confirmation of a desired lens effect is illustrated in FIG. 2. A rastophotogram is made of the calibration block, the laser beam is applied to the calibration block, and a second rastophotogram is performed to confirm the desired lens effect in the calibration block. For example, the desired lens effect is 4.00 dioptric, the amount of calibration block material that is removed at each point along the radius of the calibration block can be computed and the actual amount removed compared quantitatively and qualitatively to the effect desired. Moreover, the astigmatic and multi-zone (aspherisity) correction desired can be calibrated and measured quantitatively.

Figure 3:
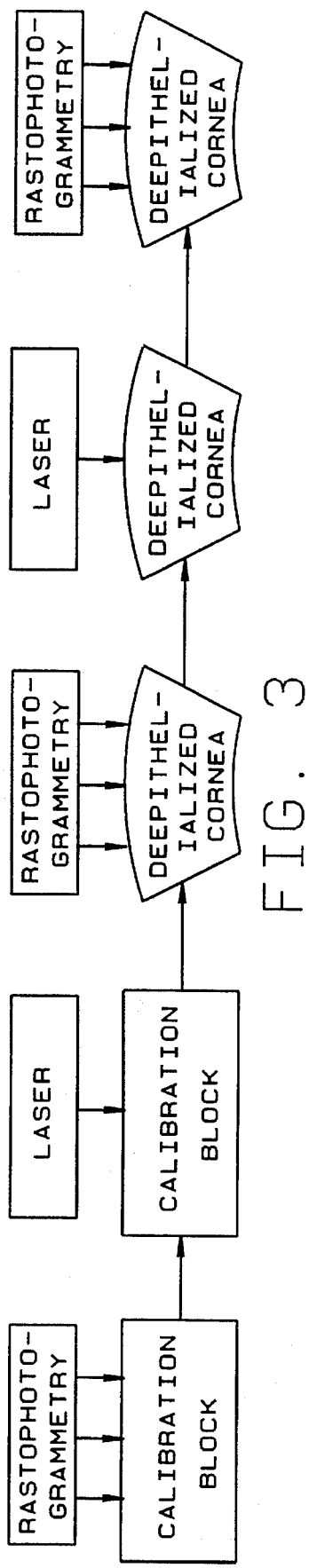
FIG. 3 is a diagram illustrating the use of rastophotogrammetry in an ophthalmological surgical procedure.

FIG. 3 illustrates the use of rastophotogrammetry in corneal surgery performed to alter the refractive index of the human cornea. As illustrated, a rastophotogram is made of a calibration block. As previously stated, the laser is applied to the calibration block to determine the amount of ablation and to determine whether or not there is unwanted lens effect. In this manner and through these steps, it can be evaluated whether the laser is properly calibrated before the laser is used on the human eye. Next, a rastophotogram is performed on a deepithelialized human cornea. The laser is then applied to the deepithelialized cornea and ablation performed. Finally a rastophotogrammetry is performed to determine if the proper refractive index of the deepithelialized cornea has been achieved. The steps may be repeated to validate repeated ablations.

As illustrated in FIG. 3, under-correction can be avoided by continuing the treatment session until the desired amount of correction is achieved. Furthermore, in order to enhance the quality of the video image at this point, a surface dye can be applied to the deepithelialized cornea. In addition, the rastophotogrammetry grid can be projected using various wave lengths and filters for optimal visualization of the projected grid.

Figure 4A:
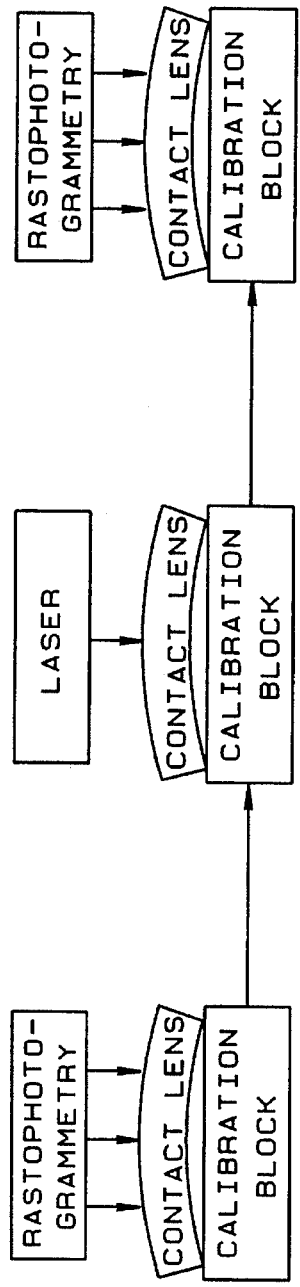
FIG. 4A is a diagram illustrating the use of rastophotogrammetry to evaluate a laser based on the effect on a contact lens of a known refractive power.

FIG. 4A illustrates the use of the rastophotogrammetry in the evaluation of the surgical laser using a contact lens of a known dioptric power. A contact lens of a known dioptric power formed from polymethylmethachrylate is fastened to a holding block, such as previously described polymethylmethachrylate calibration block. The contact lens can be constructed as an artificial cornea and can be white to fascilitate imaging with the restophotogrammetric system.

Next, rastophotogrammetry is performed on the contact lens front surface to get an accurate baseline reading of the topography of the front surface of the lens. Next, the laser is used on the front curvature of the lens. Finally, a second rastophotogram is performed to determine that the effect of the laser on the lens responds to the desired changed in the known dioptric power of the lens so that the laser can then be properly calibrated based upon the evaluation of the effect of the laser beam on the lens with known dioptric power. The steps in the procedure may be repeated to validate the calibration.

Figure 4B:
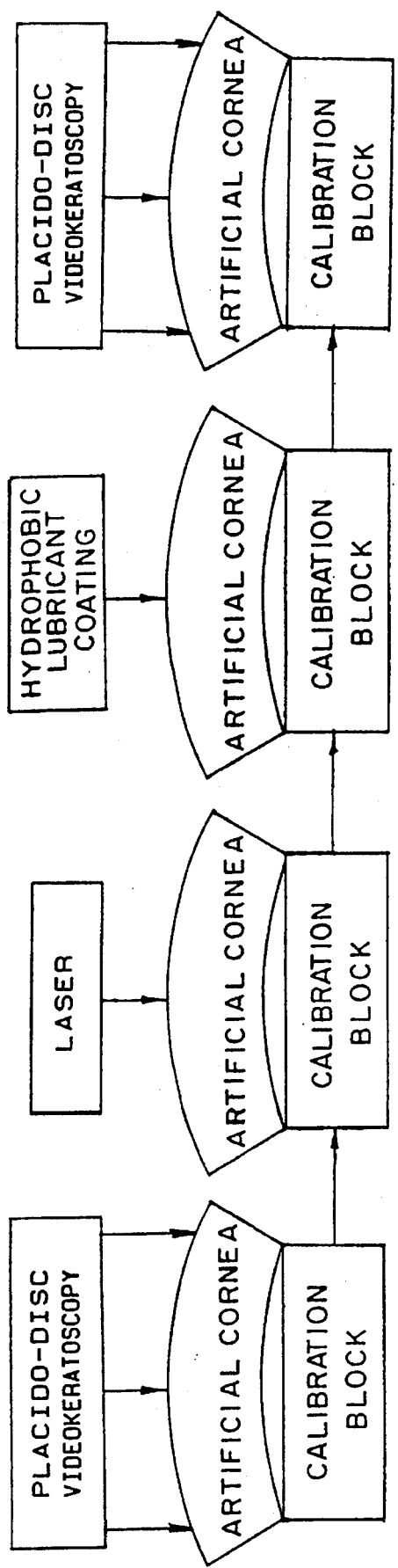
FIG. 4B is a diagram illustrating the use of Placido-disc videokeratoscopy to evaluate a laser based on the effect on an artificial cornea of a known refractive power.

FIG. 4B illustrate the use of Placido-disc videokeratoscopy in the evaluation of a surgical laser using an artificial cornea of a known dioptric power. An artificial cornea of a known dioptric formed from polymethylmethacrylate or other appropriate material is fastened to a holding block, as previously described. The artificial cornea can be black plastic to facilitate imaging with a videokeratoscope. The artificial cornea should be colored all the way through so that ablation does not penetrate the colored layer only.

Next, a Placido-disc videokeratoscope procedure is performed on the artificial cornea front surface to get a accurate baseline reading of the topography of the front surface of the cornea. A first videokeratograph of the topography is made. Next, a laser is used on the present curvature of the artificial cornea. A nonviscous, fine hydrophobic lubricant, such as a thin oil, can be placed on the ablated surface of the artificial cornea to enhance visualization since the ablated surface loses its reflectively. A second Placido-disc keratoscopy procedure is performed and a second videokeratograph is made. The first and second videokeratographs are compared to evaluate the ablating power of the laser. It will be appreciated by those skilled in the art that Placido-disc video keratoscope procedures work poorly on deepithelialized cornea right after surgery. However, the procedure works well for imaging the artificial cornea before and after ablation, as first described. Therefore, the Placido-disc keratoscopy can be used in connection with rastophotogrammetry in the surgical setting. The effect of the laser on a artificial cornea can be determined by the use of Placido-disc video keratoscopy. The laser is used to preform corneal ablation. Subsequently, rastophotogrammetry is performed an the deepithelialized cornea to determine corneal topography. Corneal ablation is performed and a repeat rastophotogram is made and compared to the first to validate the laser action.

Figure 5:
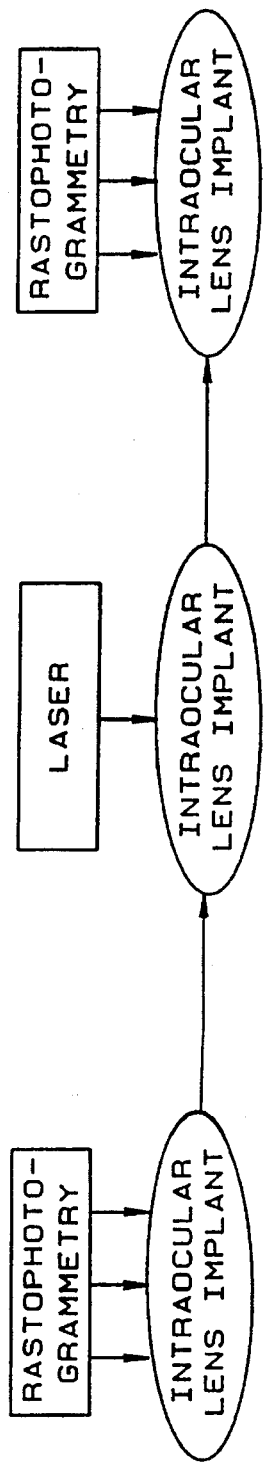
FIG. 5 is a diagram illustrating the use of rastophotogrammetry to change the refractive index of an intraoccular implant.

FIG. 5 illustrates the use of the rastophotogram to determine the effective laser adjustment of refractive index of an intraoccular implant. As illustrated, the rastophotogrammetry procedure is performed on the intraoccular implant as to determine a base line. Next, the laser beam is applied to the intraoccular lens implant to alter the curvature of the implant and thereby alter the refractive power. The second rastophotogram of the intraoccular implant is then performed to provide feedback mechanism to ascertain if the desired refractive change has been achieved. The procedure may be repeated until the desired change in refractive power is achieved.

Various changes and modifications can be made in the foregoing description and drawings within the scope of the present invention. Therefore, the foregoing description and accompanying drawings are to be interpreted as illustrative and not in a limiting sense.

Having thus described the invention, what is claimed and desired to be secured by Letters Patent is:

1. A method for evaluating surgical laser for use in ophthalmological surgery comprising the steps of:

performing a first Placido-disc video keratoscope procedure on a substrate to determine surface contour of said substrate;

making a first video keratograph;

applying a laser beam to said substrate;

ablating said substrate with said laser beam;

enhancing visualization of said substrate by applying a fine hydrophobic lubricant to said substrate;

performing a second Placido-disc video keratoscope procedure on said substrate to determine a second surface contour of said substrate after ablation;

making a second video keratograph; and evaluating said laser beam performance based upon a comparison of said second and said first video keratographs.

2. The method of claim 1 wherein said step of performing a first Placido-disc keratoscope procedure on a substrate to determine surface contour of said substrate further includes performing a first Placido-disc keratoscope procedure on an artificial cornea of known dioptric power.

* * * * *